United States Patent [19]
Ostrow

[11] Patent Number: 5,823,989
[45] Date of Patent: Oct. 20, 1998

[54] ELECTROPHORETIC CUFF APPARATUS DRUG DELIVERY SYSTEM

[75] Inventor: Alvin S. Ostrow, Raanana, Israel

[73] Assignee: Electromagnetic Bracing systems (EBS) Inc., Secaucus, N.J.

[21] Appl. No.: 636,406

[22] Filed: Apr. 23, 1996

[30] Foreign Application Priority Data

Apr. 23, 1995 [IL] Israel .......................................... 113459

[51] Int. Cl.⁶ ..................................................... A61N 1/30
[52] U.S. Cl. ............................................. 604/20; 607/153
[58] Field of Search ................ 604/20–21; 607/152–153

[56] References Cited

U.S. PATENT DOCUMENTS

| 4,729,377 | 3/1988 | Granek et al. . |
| 4,968,297 | 11/1990 | Jacobsen et al. . |
| 5,037,380 | 8/1991 | Jacobsen et al. . |

FOREIGN PATENT DOCUMENTS 0193480   9/1986   European Pat. Off. .

Primary Examiner—Mark Bockelman
Attorney, Agent, or Firm—Edward Langer, Pat. Atty.

[57] ABSTRACT

A flexible cuff for wrapping around a part of a limb, that is comprised of multiple patch units of a required size and shape to fit the body contour for applying to an area of skin. The cuff has an array of flexible (polymer) electrodes held at constant potential with alternating polarities. A network of supply tubes connected to an external liquid reservoir, provides a slow supply of a medicated fluid to each electrode.

An electric field applied through the cuff then causes the drug to be rapidly absorbed throughout the skin. The electrodes within the cuff, or applicator pads which it is comprised of, can be additionally be used for applying Transcutaneous Nerve Stimulation, and for Electrical Muscle Stimulation. Alternately, the cuff can be used to assist rehabilitation exercise therapy conditioning in combination with Electrical Muscle Stimulation.

19 Claims, 4 Drawing Sheets

ELECTROPHORETIC CUFF APPARATUS DRUG DELIVERY SYSTEM

FIELD OF THE INVENTION

The present invention relates generally to medical appliances and especially to the application of a uniform system of an electrophoretic pharmaceutical delivery cuff apparatus system where electrically charged porous pads are in fluid communication with a drug medium.

BACKGROUND OF THE INVENTION

The use of iontophoresis and electrotherapy for drug delivery has been known and recognized as an acceptable form of treatment. Prior devices utilizing iontophoresis and / or electrophoresis were unable to simultaneously treat large areas systematically in an anatomical circumference or be incorporated under cast or braces with the exception of the inventor's previous U.S. Pat. No. #5,344,384.

Furthermore, the previously known devices did not provide the availability of multiple treatment protocols.

Many iontophoretic transdermal drug delivery devices have been described in the patent literature, including U.S. Pat. Nos:

5,387,189 to Gory et al.;
5,358,483 Sibalis;
5,356,632 Gross et al.;
5,312,325 Sibalis;
5,279,544 Gross et al.;
5,167,479 Sibalis;
5,156,591 Gross et al.;
5,135,479 Sibalis et al.;
5,088,977 Sibalis;
5,057,072 Phipps;
5,053,001 Reller et al.;
4,942,883 Newman;
4,752,285 Patelenz et al.;
4,734,090 Sibalis;
4,731,049 Parsi;
4,622,031 Sibalis;
4,325,367 Tapper; and
4,164,226 Tapper.

OBJECTS AND BRIEF SUMMARY OF THE INVENTION

The electrophoretic cuff apparatus of the present invention encompasses the construction of a preform applicator wrap for applying an electrical current to electrophoretically porous, electrically conductive applicator pads to pass a slow drip liquid drug medium through the skin and surface tissues. The applicator wrap is externally self supported contiguous to a body surface to form a preform wrap or cuff.

In particular, the present invention concerns an electrotherapy apparatus incorporated within or without a cast or orthotic brace or preform that delivers ancillary treatment modalities which are provided by an optional Neuromuscular Electrostimulation, Transcutaneous Nerve Stimulation (T.E.N.S.), and Interferential Electrotherapy component. The preform forms a "cuff" that can be wrapped around the body in different sizes and sections for easy treatment of large and small anatomical areas. The cuff is connected by a Velcro attachment to latch on the sections connected by male and female electrical and fluid flow connectors respectively to deliver the fluid medium and electrical charge.

The construction of the apparatus is important for consistent uniform drug therapy around the circumference of a body part to increase efficiency of drug therapy application. When the apparatus is not used for drug delivery, it can be applied and worn in conjunction simultaneously while the patient is exercising or conducting activities of daily living.

The cuff wrap matrix is formed of waterproof molded flexible plastic, Styrofoam, or canvas -like material with male and female electrical and fluid flow connectors to accommodate a continuous hook-up for additional preform patches of various required sizes and shapes to encompass the circumference of a desired targeted treatment area, thereby creating a "cuff" or wrap around any anatomical body part.

The wrap is provided with a network array of electrically conductive porous polymer electrodes providing a "checkerboard" pattern of alternating positive and negative polarities.

A feature regarding the present invention of the electrophoretic cuff is that it can have multiple uses beyond its use for introducing drugs transdermally. Thus, the present invention provides, in a versatile fashion, a variety of therapeutic benefits and applications with electrical energy modes for nerve stimulation, pain sedation, and for the prevention of atrophy. Additionally, when configured as a therapeutic garment, the mode of Electrical Muscular Stimulation (EMS) can be introduced during physical therapy exercises, weight training for neurologically impaired and atrophic muscles, etc.

It should be apparent that the multi-modal nature of this apparatus cover a broad spectrum of treatment protocols including the treating of injuries to soft tissues as well as arthritis of joints at selected locations on the human or mammalian body.

The cuff provides a consistent supply of medication by titration throughout the porous polymer electrode pads to bathe the body part in a continuous fluid within a circumference, whereas other electrical transdermal drug delivery methods are not as easily accessible or applicable. This system also allows for transdermal drug treatment simultaneously to more than one location where greater medical attention is needed. In addition, a non-medicated fluid can also be used to moisten the porous electrodes as an electrolyte to assist electrical conductivity when the apparatus is being used for purposes other than for drug delivery.

In addition, the cuff applies continuous fluid medium from an external reservoir similar to intravenous (I.V.) applicators without the use of a syringe. The cuff can be used as an option to replace traditional methods of postoperative analgesia such as intramuscular injections. The cuff has benefits for those patients who dislike needle injections—especially children.

Furthermore, the delivery of drugs transdermally is regulated and monitored through a computer chip and "siphon" distribution system that records titration rate, amount and dosage of medication supplied.

In view of the foregoing, it should be apparent that the present invention provides many advantages and overcomes many of the shortcomings and disadvantages of the prior art, while providing an improved apparatus.

Having thus summarized the invention, it will be seen that is an object thereof to provide a electrophoretic cuff apparatus of the general character described herein which is not subject to the aforementioned deficiencies.

Another object of this invention is to provide a electrophoretic cuff apparatus that can fit under a cast or brace. A foam fabric used on the superior external surface of the apparatus adding to patient comfort.

A further object of this invention is to provide a electrophoretic cuff apparatus having selective curative regimens that can be applied severally or jointly.

A still further object of this invention is to provide a electrophoretic cuff apparatus that can be comfortably worn by the patient, as a lightweight, portable device that is cost effective to manufacture.

Another object of this invention is the capability to delivery any drug in a fluid medium having either a positive or negative molecular valence through the skin iontophoretically. Many drugs have been formulated for use in iontophoretic systems and others are being experimented and developed for the feasibility of their delivery for commercial use in the pharmaceutical industry by employing iontophoresis (e.g., nicotine antihistamines, beta-blocker, calcium channel blockers, non-steroidal, anti-inflammatory drugs, contraceptives, anti-arrhythmic drugs, insulin, antivirals, hormones, alpha-interferon, and cancer chemotherapeutic agents.)

Yet another object of this invention is to optionally produce a selected alternating positive or negative electrical charge from a controlled power source / console switch, thereby creating the electrical field polarity which is responsible for providing the "ionic drive" mechanism needed to modulate either anode or cathode drug delivery within the electrophoretic pads. The ionic drive mechanism is the force behind the electrochemical phenomenon of iontophoresis required to propel, infuse, and deliver a pharmaceutical medium in accordance with its polar molecular valence through the skin's surface by means of electroosmosis. The success of administering the fluid medium depends on the negative or positive valence of the pharmaceutical medium for anode or cathode delivery. Additional features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENTS

With specific reference now to the figures in detail, it is stressed that the particulars shown are by way of example and for the purpose of illustrative discussion of the preferred embodiments of the present invention only, and are presented in the cause of providing what is believed to be the most useful description principles and conceptual aspects of the invention based upon the medical literature. In this regard, no attempt is made to show structural aspects of the invention in more detail than is necessary for a fundamental understanding of the invention, the description taken with the drawings making it apparent to those skilled in the art how the several forms of the invention may be embodied in practice.

Figure 1:
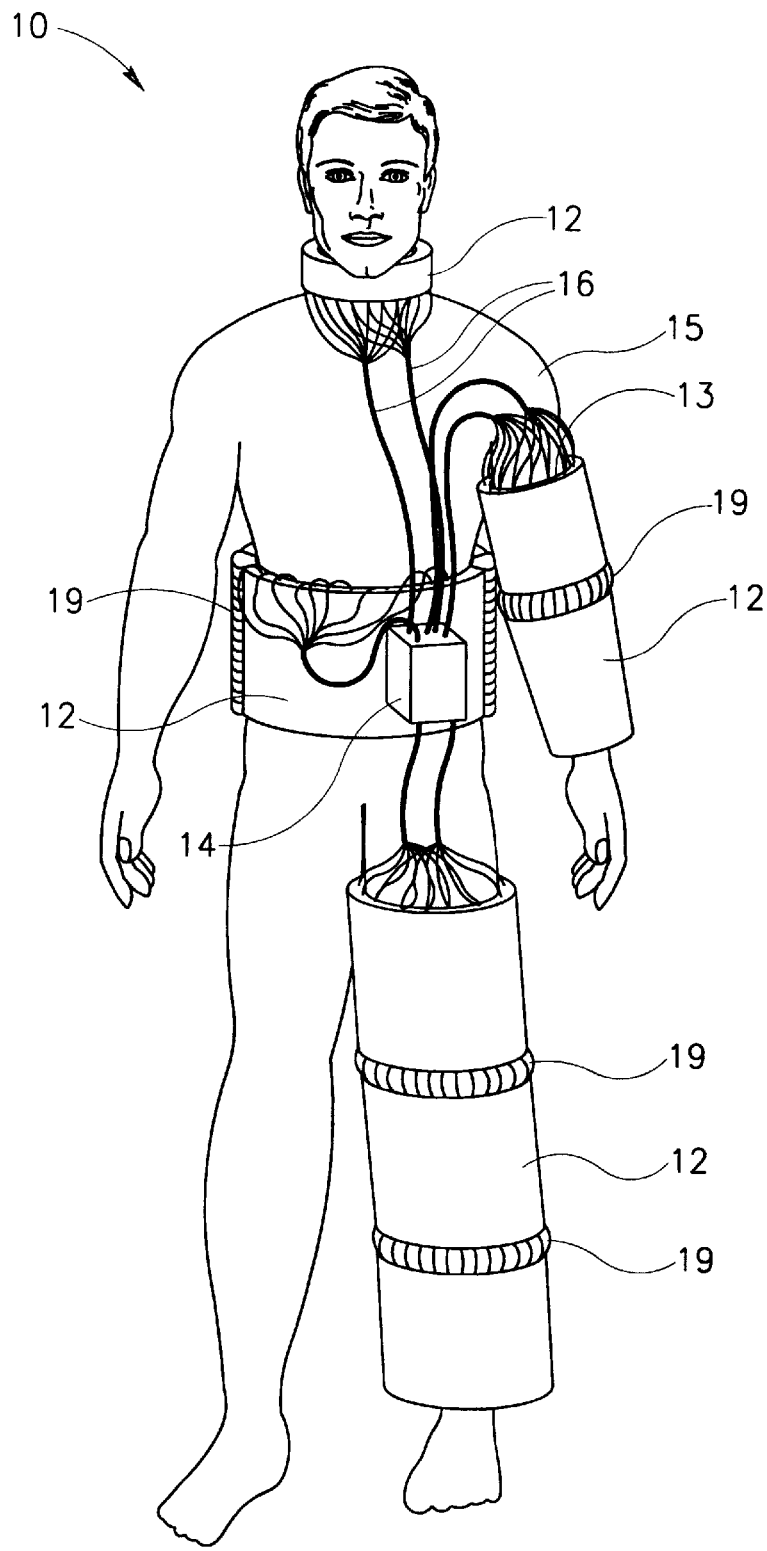
FIG. 1 is a front elevational view pictorially illustrating the electrophoretic cuff apparatus of the invention as applied to selected portions of the human body including neck, arm, lower back and leg.

Referring now to FIG. 1, there is illustrated a pictorial representation of a electrophoretic cuff apparatus 10 in accordance with this invention. The electrophoretic cuff apparatus 10 is typically shown at selected anatomical locations on a human body.

The apparatus 10 is comprised of a flexible cuff 12 for wrapping around of a body part or limb, a portable operating console 14 that incorporates a power supply source and a cable harness 16 for conductively coupling the console 14 to the cuff 12.

Figure 3:
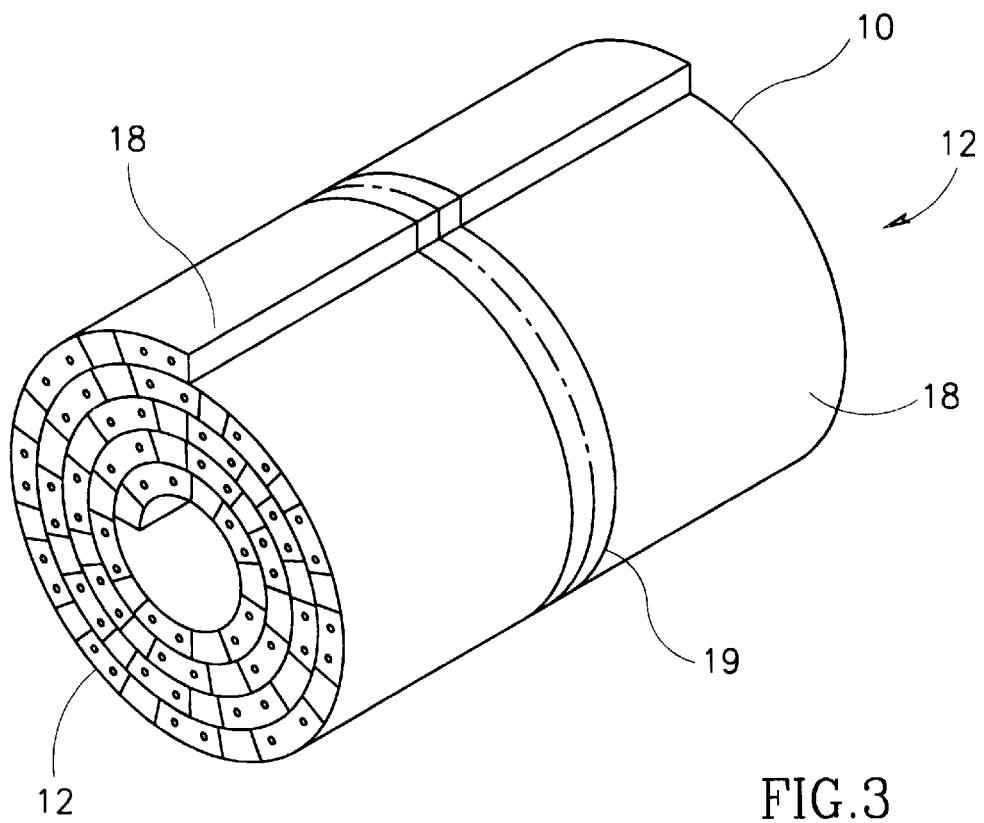
FIG. 3 is a perspective view of a portion of a patch connected to other patches forming a cuff in a stored configuration.

The flexible cuff wrap 12, as best shown in FIGS. 1 & 3, is fabricated from a plastic and or canvas garment-like fabric having linked patches 18 connected by Velcro strapping 19 as a closure for securing the cuff 12 against afflicted areas on the patient's body as for example as shown in FIG. 1. The patch 18 provides the required flexibility when applied around or on a body part, and is compliant when it is attached to another patch 18 by the Velcro 19 strapping and connected by electrical connector plugs 52, 53 (FIG. 4a) and fluid-flow connectors 21 (FIG. 4c).

Figure 2:
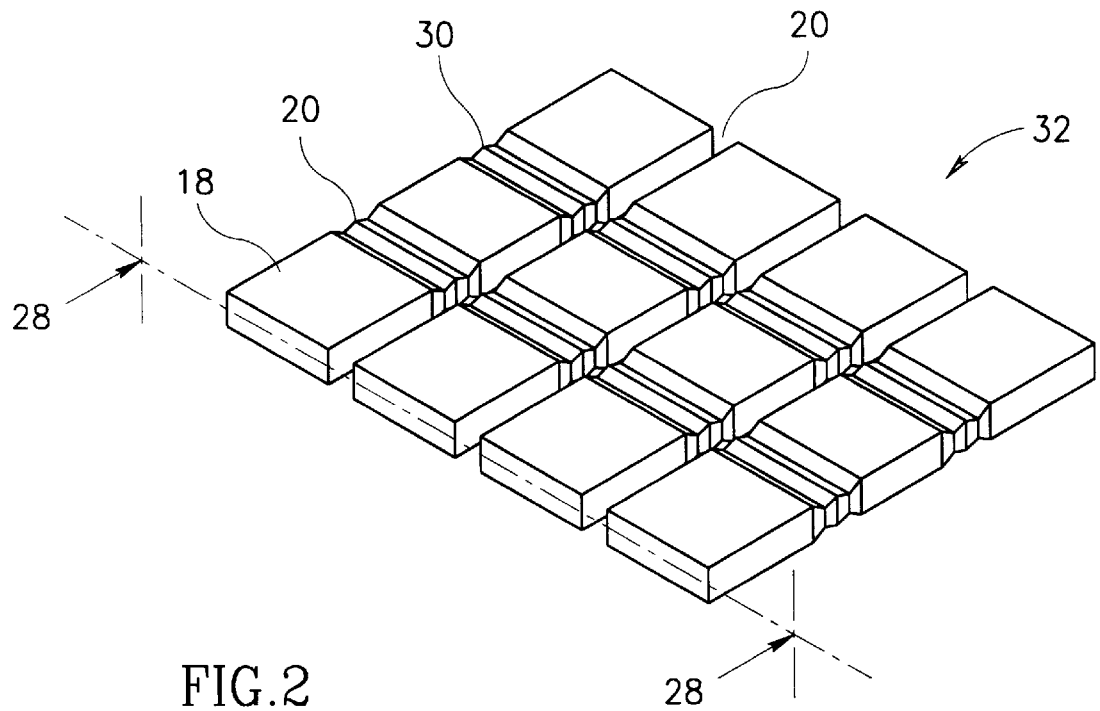
FIG. 2 is a perspective view of a portion of an applicator patch in conjunction with the apparatus of the invention illustrating a grid of electrode pads.

In FIG. 2, a plurality of porous electrodes 32 which are made of polymer or equivalent materials are positioned within each patch 18 such that a longitudinal axis 28 of the electrodes 32 is perpendicular to a transverse axis 30 of the cuff 12. A contact surface 13 of the cuff 12 is intended for placement contiguous to the patient's skin 15. By way of example, the electrodes 32, such as shown in FIG. 4, are rectangular approximately ⅜ in. on each side and are spaced apart at point 20 approximately 2:1 ratio center to center to provide about (4) electrodes 32, per square in. within the cuff 12. Furthermore, the electrodes 32 can be embedded in the plastic material during the manufacturing process and are thus secured in place by surrounding plastic material. Alternatively, the electrophoretic tubing 66 and tubing connectors 21 pass on top of, and are superior to the surface 34 of the electrodes 32 simultaneously as they connect with the electrodes via a duct system 67 as shown in FIG. 5.

Further in connection with the fabrication of the cuff wrap 12, it should be observed that before the electrodes are fixed into position, inside wiring 61 and electrophoretic tubing 66 are placed against the inside face of a waterproof substrate and / or canvas-like fabric forming the apparatus matrix, to prevent "leakage" of medicated or non-medicated fluid outside the aforementioned cuff.

Figure 4A:
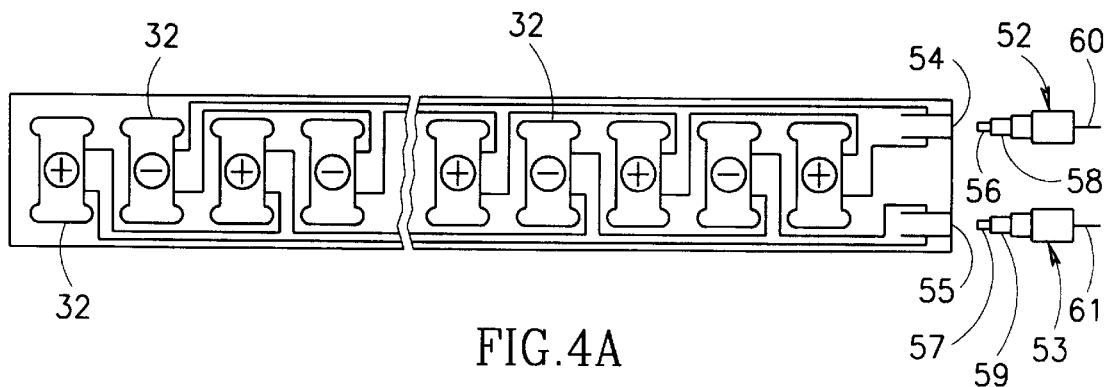
FIG. 4a is an elevational view, to enlarged scale, of a portion of the applicator cuff showing the electrical circuitry for energizing the electrode pads.
Figure 4B:
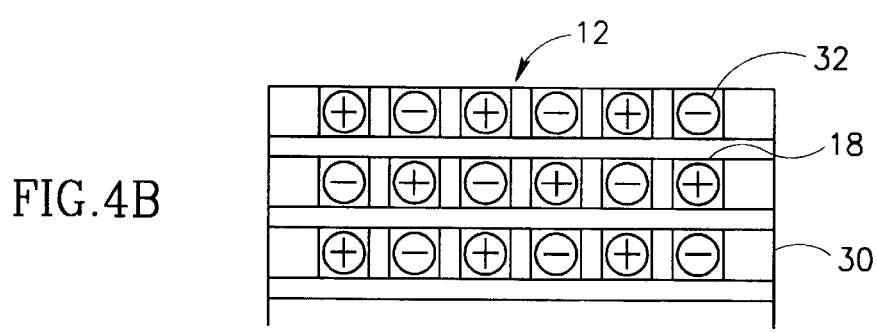
FIG. 4b is a perspective view of a portion of an applicator wrap used in conjunction with the apparatus of the invention illustrating a "checkerboard" pattern of positive and negative electrically charged electrodes.
Figure 4C:
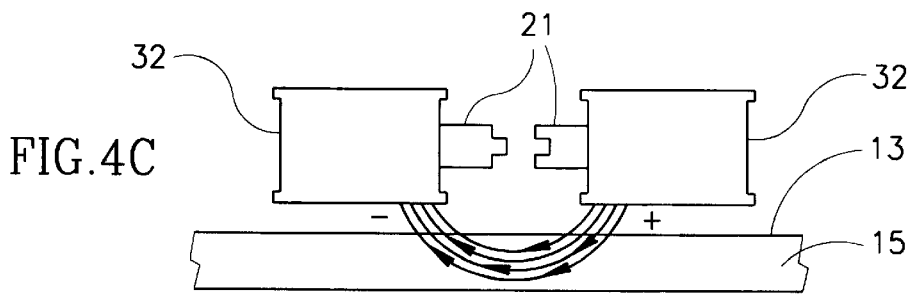
FIG. 4c is an elevational view showing the combined lines of positive and negative electron flow or the electrical charge of opposite polarity associated with the apparatus.
Figure 5:
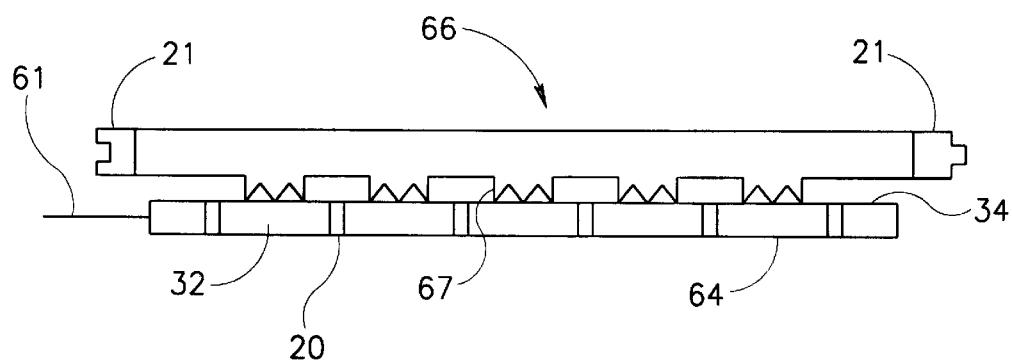
FIG. 5 shows a schematic drawing of a side view cross section showing the alternating polarities of the electrodes and supply tubes for delivering the fluid medium to the electrodes via a system of branching ducts.

Referring once again to the electrodes 32, it will be noted in FIG. 4a that the wiring sequence for each electrode 32 provides for a current flow through adjacent electrodes 32 in opposite directions to thereby generate a "checkerboard" of electrical currents of alternate polarities as graphically depicted in FIG. 4b. This is accomplished by conductively coupling the wiring in two circuits as will be further described herein. It will be appreciated by those skilled in the art that the inside wiring within the electrode patch can be replaced by a modified electrode pad comprising an electroconductive polymer membrane. A wire harness 16 is conductively coupled to the applicator patches 18 by a set of (two-conductor) connector plugs 52, 53 that are accommodatingly received within a corresponding set of sockets 54, 55.

Referring to FIG. 4a, it will be seen that the set of plugs 52, 53 contain two conductors 56, 58, 60 and 57, 59, 61, respectively. The conductors 56, 58, and 57, 59, when inserted within the respective sockets 54, 55 complete circuits for energizing the electrodes. As seen in FIG. 4c, it will be noted that when the current flows in a clockwise direction in the electrodes 32 in one circuit defined by plug 52, the current will correspondingly flow in a counterclockwise direction through the electrodes within the other circuit defined by plug 53.

Figure 6:
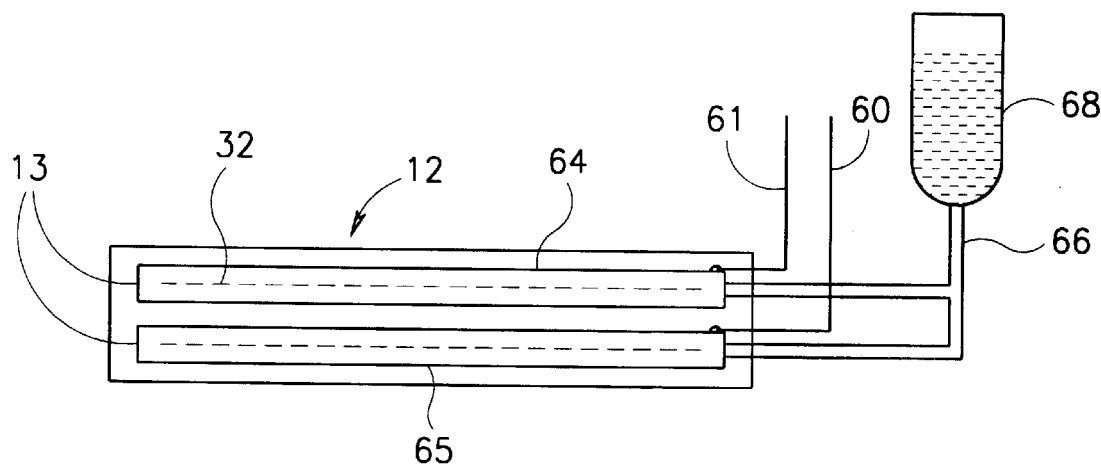
FIG. 6 is a cross-sectional view of an electrophoretic pharmaceutical delivery system with a fluid reservoir connecting to the apparatus.

Referring now to FIG. 6, there is shown an electrophoretic pharmaceutical delivery system with a fluid reservoir. The electrophoretic cuff 10 can induce a pharmaceutical fluid flow when simultaneously placed under a cast or brace with additional treatment modalities of electrostimulation. In addition, pain sedation can be provided by nerve stimulation analgesia, and galvanic muscle strengthening can be provided by producing muscle contraction that deters the onset of atrophy in a body part. The electrostimulation regimen is also effective for reversing the degenerative affects of atrophia.

This aspect of the invention includes the incorporation of a set of conductive stimulator pads 64, 65. The stimulator pads 64, 65 are applied to the contact surface 13, of the cuff wrap 12. The conductors 60, 61 provide the respective pads 64, 65 with opposite charges of DC current. When the cuff 12 is placed on the patient, the stimulator pads 64, 65 are in direct contact with the skin surface. The preferred power supply 46 is an electrochemical cell such as a commercially available nickel cadmium or lithium 9 volt rechargeable battery. The battery is housed within the console 14. With reference to FIG. 1 it will be seen that a pulse generator 55 is included within the console 14. The generator 55 supplies DC electrical power for electrostimulation and for the electrophoretic pharmaceutical delivery system.

It should be noted that the pulse generator 55 provides a direct current of low frequency having sinusoidal and trapezoidal waveform pulses at between 1–200 hertz. It should be understood however that the pulse generator 55 can be modulated in accordance with the desired electrostimulation therapy.

The previously described muscular electrostimulation and interferential microcurrent therapy can be used independently or in combination with the electrophoretic therapy delivery system.

With regard to the electrophoretic pharmaceutical delivery system, a computerized chip and computer monitor 70 in a fluid distribution system monitors and supplies the medicated fluid at various desired titration rates of ml/per second, and regulates fluid flow from an external bag reservoir 68 to increase efficiency to perform iontophoresis.

Figure 7:
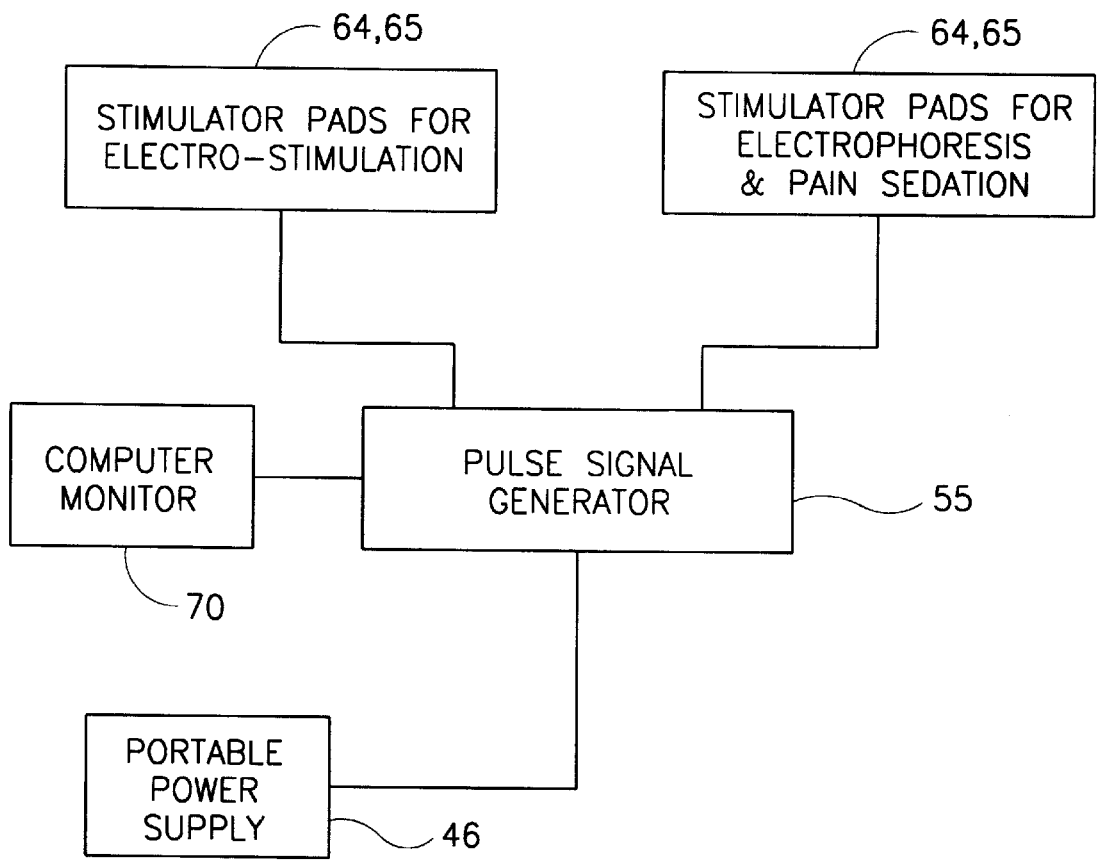
FIG. 7 is a block diagram of the invention showing a electrical circuit of the electrode pads divided into convenient functional sections.

The purpose of the iontophoresis is to utilize an electrical field to influence the transfer and metabolism of the drug medium in to the patient's body as shown in FIG. 6 & 7. For this purpose, the stimulator pads 64, 65 include a porous material that is connected by a network of tubing 66 supplied with a selected drug medium from a reservoir 68 through a gravity feed system. It should be further noted that the stimulator pads 64, 65 are thus electrically energized by the pulse generator 55 through the respective conductors 60, 61 and that each of the pads 64, 65 will at all times be oppositely charged. In operation, pads 64, 65 provide the function of receiving the pharmaceutical medium from the branch tubing 66. The fluid medium is distributed throughout the pads 64, 65 by capillary action. The application of the electrical current provides an ionization effect producing a more effective delivery path to the patient. This is particularly advantageous when a conventional cast or brace has been placed over the electrophoretic cuff apparatus 10 and thus the afflicted area is otherwise inaccessible to direct drug therapy.

The signals utilized in connection with the electrophoretic system include DC current modulation having a trapezoidal, square and sinusoidal wave pulses from 0–50 volts with alternating and continuous pulses modulated at between 1 to 200 hertz and the electrical current ranging from 0–50 mA, with a current range from 0–15 mA responsible to perform iontophoresis. For iontophoresis, the mode can vary 50% on, 50% off or as desired. For neuromuscular stimulation, the pulses have a 20% to 30% "off" and 70% to 80% "on" timing for maximum effectiveness.

It should be further observed that this treatment mode also provides, as an adjunct, transcutaneous nerve stimulation for pain sedation. In this regard, the transcutaneous nerve stimulation can be effected concurrently with or independently of the iontophoretic drug therapy.

It should also be further observed that low frequency, low intensity interferential currents are used to treat edema or swelling associated with injuries and can be used in electrodes provided within this system.

The apparatus forms a cuff that allows patients with atrophy to perform passive and active exercise while wearing it.

It should be further observed that the network of reservoir and tubing can be optionally use to distribute inert liquids that provide thermal fluid therapy, hot or cold, to a target area within the patch or cuff if so desired. A temperature gauge attached to the reservoir measures the temperature in Celsius and/or Fahrenheit. It is well known in the literature that temperature has an influence on transdermal transport of drugs during iontophoresis.

It should thus be apparent that a clinician or patient can choose desired options of the aforementioned therapies singularly or in combination using the operating console 14.

It will be evident to those skilled in the art that the apparatus is not limited to the details of the foregoing illustrated embodiments and that the present may be embodied in their specific forms without departing from the spirit or essential attributes thereof.

The present embodiment is therefore to be considered in all respects as illustrative and not in a restrictive sense. The scope of the being indicated by the appended claims rather than by the forgoing description and all changes which come within the meaning and range of equivalency of the claims are therefore intended to be embraced therein.

I claim:

1. An electrophoretic cuff apparatus comprising:
    an applicator wrap of single or multiple connecting patch units each containing a plurality of electrophoretic electrode applicator pads;
    means for simultaneously generating, an electric current in each of said applicator pads, and
    a network of tubing adjacent to a surface of said applicator pads for delivering a selected pharmaceutical medium to said applicator pads, said applicator pads being selectively energized by said electric current for providing drug treatment therapy.

2. The electrophoretic cuff apparatus as claimed in claim 1 comprising a plurality of said connecting patch units wherein each of said connecting patch units has a number of connectors to form a wrap of a required size and shape to fit the body contour, each of said patch units being separately linked by Velcro fastening means adapted to surround an injuired or diseased body member.

3. The electrophoretic cuff apparatus as claimed in claim 1 further including an electrostimulation component having at least two stimulator pads, said stimulator pads being adapted for placement on the surface of a patient's skin, said pads further being selectively energized by said generating means supplying low frequency pulsed DC current providing muscle stimulation.

4. The electrophoretic cuff apparatus as claimed in claim 1 wherein said current generating means comprises a portable power source, said power source including a pulse signal generator to generate said electric current as a DC current modulated in the format of at least one of trapezoidal, square and sinusoidal wave pulses from 0–50 volts with alternating and continuous pulses modulated at between 50 to 200 Hz and the electrical current ranging from 0–50 mA, with in a current rage 0–15 mA.

5. The electrophoretic cuff apparatus as claimed in claim 4 wherein said pulses are generated individually.

6. The electrophoretic cuff apparatus as claimed in claim 4 wherein said pulses are generated in combination.

7. The electrophoretic apparatus as claimed in claim 1; wherein each of said applicator pads is provided as a porous electroconductive polymer electrode pad which are adjacently positioned with opposite polarity, and are connected by electrical wiring.

8. The electrophoretic apparatus as claimed in claim 1 wherein each of said applicator pads is connected to a plurality of male and female electrophoretic tubing connectors that can be attached and hooked up to the said tubing network.

9. This applicator cuff apparatus as claimed in claim 1 wherein said applicator wrap and electrode pads are formed of a flexible porous electroconductive polymer membrane material.

10. The electrophoretic cuff apparatus as claimed in claim 1 wherein said applicator wrap is adapted for use as as an electrotherapeutic exercise cuff device worn as a therapeutic garment by at least one of ambulatory and non-ambulatory patients.

11. The electrophoretic cuff apparatus as claimed in claim 1 wherein said applicator pads are connected to a controlled slow drip liquid drug reservoir through said tubing network with a system of duct distribution to each and every individual porous electrode pad to deliver a drug through the skin and surface tissues.

12. The electrophoretic cuff apparatus of claim 8 further comprising a computerized control device for regulating flow from said slow drip liquid reservoir through said tubing network.

13. The electrophoretic cuff apparatus of claim 12 wherein said computerized control device comprises a display read-out of a flow rate of said liquid.

14. A method of providing electrophoretic drug treatment therapy comprising the steps of providing an electrophoretic cuff apparatus comprising:
    an applicator wrap of single or multiple connecting patch units each containing a plurality of electrophoretic electrode applicator pads, wherein said applicator wrap and said applicator pads are formed of a flexible porous electroconductive polymer membrane material;
    means for simultaneously generating an electric current in each of said applicator pads; and
    a network of tubing adjacent to a surface of said applicator pads; delivering a selected pharmaceutical medium to said applicator pads, said applicator pads being connected to a controlled slow drip liquid drug reservoir through said network of tubing with a system of duct distribution to each and every individual applicator pad; and selectively energizing said applicator pads by said electric current to provide said drug treatment therapy through the skin and surface tissues.

15. The method of claim 14 wherein said step of selectively energizing said applicator pads establishes at least one of anode and cathode drug delivery modes.

16. The method of claim 14 wherein said step of selective energizing said applicator pads provides a DC current modulated in a format of at least one of trapezoidal, square and sinusoidal wave pulses from 0–50 volts with alternating and continuous pulses modulated between 50 to 200 Hz and the electrical current ranging from 0–50 mA, within a current range from 0–15 mA.

17. The method of claim 16 wherein said pulses are generated individually.

18. The method of claim 16 wherein said pulses are generated in combination.

19. An electrophoretic cuff apparatus comprising:
    an applicator wrap of single or multiple connecting patch units each containing a plurality of electrophoretic electrode applicator pads, wherein said applicator wrap and said applicator pads are formed of a flexible porous electroconductive polymer membrane material;
    means for simultaneously generating an electric current in each of said applicator pads; and
    a network of tubing adjacent to a surface of said applicator pads for delivering a selected pharmaceutical medium to said applicator pads, wherein said applicator pads, are connected to a controlled slow drip liquid drug reservoir through said network of tubing with a system of duct distribution to each and every individual applicator pad, said applicator pads being selectively energized by said electric current for providing drug treatment therapy through the skin and surface tissues.

* * * * *